(12) United States Patent
Lewis, Jr. et al.

(10) Patent No.: US 9,480,863 B2
(45) Date of Patent: Nov. 1, 2016

(54) ULTRASOUND COUPLING DEVICE

(75) Inventors: George K. Lewis, Jr., Ithaca, NY (US); Bryant Guffey, Ithaca, NY (US)

(73) Assignee: ZetrOZ Systems, LLC, Trumbull, CT (US)

( * ) Notice: Subject to any disclaimer, the term of this patent is extended or adjusted under 35 U.S.C. 154(b) by 783 days.

(21) Appl. No.: 13/519,953

(22) PCT Filed: Jan. 3, 2011

(86) PCT No.: PCT/US2011/020052
§ 371 (c)(1),
(2), (4) Date: Jun. 29, 2012

(87) PCT Pub. No.: WO2011/082402
PCT Pub. Date: Jul. 7, 2011

(65) Prior Publication Data
US 2012/0277640 A1    Nov. 1, 2012

Related U.S. Application Data

(60) Provisional application No. 61/291,804, filed on Dec. 31, 2009, provisional application No. 61/291,779, filed on Dec. 31, 2009, provisional application No. 61/291,732, filed on Dec. 31, 2009.

(51) Int. Cl.
*A61N 7/00* (2006.01)
*A61B 8/00* (2006.01)
*A61B 17/225* (2006.01)

(52) U.S. Cl.
CPC ............... *A61N 7/00* (2013.01); *A61B 8/4227* (2013.01); *A61B 8/4236* (2013.01);
(Continued)

(58) Field of Classification Search
CPC .................................. A61B 8/00; A61B 8/14

USPC ........................................................... 601/2
See application file for complete search history.

(56) References Cited

U.S. PATENT DOCUMENTS 4,383,529 A    5/1983    Webster
4,787,888 A    11/1988   Fox
(Continued)

FOREIGN PATENT DOCUMENTS

JP            3063071           3/1991

OTHER PUBLICATIONS

International Search Report and Written Opinion issued in PCT/US2011/020052, mailed Sep. 27, 2011.

*Primary Examiner* — Joel F Brutus
(74) *Attorney, Agent, or Firm* — FisherBroyles, LLP; Andrew K. Gonsalves, Esq.

(57) ABSTRACT

The present invention relates to an ultrasound coupling device for use with various ultrasound transducers, systems, and applications. The coupling device includes a coupling compartment comprising a chamber having a continuous side wall and an opening on a first end. The continuous side wall is configured to hold a low-profile ultrasound transducer within the chamber so that a front ultrasound emitting surface of the low-profile ultrasound transducer faces outward toward the chamber opening. The front ultrasound emitting surface is configured to control the direction and wave pattern of ultrasonic energy emitted from the transducer. The continuous side wall is also configured to hold a quantity of an ultrasound conductive medium within the chamber and is operative to keep the ultrasound conductive medium in simultaneous contact with a surface of a subject and with at least a portion of the front ultrasound emitting surface of the transducer. The present invention also relates to an ultrasound apparatus, kit, and methods of using the ultrasound coupling device, apparatus, and kit.

17 Claims, 18 Drawing Sheets

(52) U.S. Cl.
CPC ........ *A61B 8/4281* (2013.01); *A61B 17/2251* (2013.01); *A61B 2017/2253* (2013.01); *A61N 2007/0078* (2013.01); *Y10T 29/49005* (2015.01)

(56) References Cited

U.S. PATENT DOCUMENTS

| | | |
|---|---|---|
| 5,212,988 A | 5/1993 | White et al. |
| 5,271,406 A * | 12/1993 | Ganguly et al. .............. 600/472 |
| 5,394,877 A * | 3/1995 | Orr et al. ....................... 600/459 |
| 5,494,038 A | 2/1996 | Wang et al. |
| 5,626,554 A | 5/1997 | Ryaby et al. |
| 5,628,730 A | 5/1997 | Shapland et al. |
| 5,770,801 A | 6/1998 | Wang et al. |
| 5,997,481 A | 12/1999 | Adams et al. |
| 6,477,410 B1 | 11/2002 | Henley et al. |
| 6,937,893 B2 | 8/2005 | Danz et al. |
| 7,283,874 B2 | 10/2007 | Penner |
| 2002/0156415 A1 | 10/2002 | Redding |
| 2003/0149359 A1 * | 8/2003 | Smith ........................... 600/437 |
| 2003/0171700 A1 * | 9/2003 | Martin et al. ...................... 601/2 |
| 2003/0233045 A1 * | 12/2003 | Vaezy et al. ................... 600/437 |
| 2005/0165393 A1 | 7/2005 | Eppstein |
| 2005/0215901 A1 | 9/2005 | Anderson et al. |
| 2006/0015058 A1 | 1/2006 | Kellogg et al. |
| 2006/0184070 A1 | 8/2006 | Hansmann et al. |
| 2006/0264751 A1 | 11/2006 | Wendelken et al. |
| 2008/0033292 A1 | 2/2008 | Shafran |
| 2008/0139944 A1 | 6/2008 | Weymer et al. |
| 2008/0140026 A1 | 6/2008 | Sliwa et al. |
| 2008/0195003 A1 | 8/2008 | Sliwa et al. |
| 2008/0200810 A1 | 8/2008 | Buchalter |
| 2009/0112133 A1 | 4/2009 | Deisseroth et al. |
| 2010/0132450 A1 | 6/2010 | Pomerantz et al. |
| 2010/0152644 A1 | 6/2010 | Pesach et al. |

* cited by examiner

ULTRASOUND COUPLING DEVICE

CROSS-REFERENCE TO RELATED APPLICATIONS

This application is a U.S. National Phase filing under 35 U.S.C. 371 of International Application No. PCT/US2011/020052, filed Jan. 3, 2011, and published as WO 2011/082402 on Jul. 7, 2011, which claims benefit of priority from U.S. Provisional Patent Application Ser. No. 61/291,732, filed Dec. 31, 2009, U.S. Provisional Patent Application Ser. No. 61/291,779, filed Dec. 31, 2009, and U.S. Provisional Patent Application Ser. No. 61/291,804, filed Dec. 31, 2009. The entire contents of each of the prior applications are incorporated herein by reference in their entirety.

FIELD OF THE INVENTION

The present invention relates to an ultrasound coupling device, ultrasound apparatus, ultrasound kit, and methods of using the device, apparatus, and kit in various ultrasound applications.

BACKGROUND OF THE INVENTION

Traditional therapeutic ultrasound generation technologies have a number of deficiencies that prohibit their use in portable ultrasound delivery devices. For example, current therapeutic ultrasound generation technologies are generally, at the smallest, shoebox-sized devices that include a user interface, power generation circuitry, and a separate transducer attached via a hand wand. The devices vary in shape and size, but generally are 6-20 pounds. Such devices also require wall power and administer ultrasound energies from 0-4 Watts and at frequencies of from 1-3 MHz. The energy from the transducers of such devices is applied to penetrate into the tissue and administer ultrasound. Traditional ultrasound therapies are for a short duration (e.g., 5-20 minutes). Other purported therapeutic ultrasound technologies purport to be portable, but are capable of producing only surface ultrasound waves.

Further, therapeutic ultrasound devices are generally not able to be used for long periods, due to safety concerns, the non-portable size of the devices or the need for external power sources. Thus, among other deficiencies in the art, there is a need for portable therapeutic ultrasound devices that are able to safely deliver ultrasound energy deep into tissue.

Previous attempts to provide bandages and other coupling devices for use with therapeutic ultrasound technologies have been reported. See, e.g., U.S. Pat. No. 4,787,888, U.S. Pat. No. 7,211,060, and U.S. Patent Application Publication No. US-2008/0200810. However, the ultrasound bandages or coupling devices provided in the art to date are insufficient for use with portable therapeutic ultrasound systems that are able to deliver ultrasound energy deep within tissue and that can be used for long periods of time.

There is also a need for ultrasound coupling devices that can be used with all types of therapeutic ultrasound transducers, and that can enhance the efficiency of therapeutic ultrasound transmission to a subject.

The present invention is directed to overcoming these and other deficiencies in the art.

SUMMARY OF THE INVENTION

In one aspect, the present invention relates to an ultrasound coupling device for use with various ultrasound transducers, systems, and applications. The ultrasound coupling device includes a coupling compartment, which in turn includes a chamber having a continuous side wall and an opening on a first end of the chamber. The continuous side wall is configured to hold a low-profile ultrasound transducer within the chamber so that a front ultrasound emitting surface of the low-profile ultrasound transducer faces outward toward the chamber opening. The front ultrasound emitting surface is configured to control the direction and wave pattern of ultrasonic energy emitted from the low-profile ultrasound transducer. The continuous side wall is also configured to hold a quantity of an ultrasound conductive medium within the chamber and is operative to keep the ultrasound conductive medium in simultaneous contact with a surface of a subject and with at least a portion of the front ultrasound emitting surface of the low-profile ultrasound transducer. Methods of making and using the ultrasound coupling device of the present invention are described and illustrated herein.

In another aspect, the present invention relates to an ultrasound apparatus for use with various ultrasound applications. The ultrasound apparatus includes at least one low-profile ultrasound transducer and at least one ultrasound coupling device as described herein. The at least one ultrasound coupling device is operatively coupled to the at least one low-profile ultrasound transducer, thereby forming a transducer/coupling device unit. Various energy generating modules (e.g., portable power devices) can be used to supply electric energy to the at least one low-profile ultrasound transducer, which in turn produces ultrasonic energy for various ultrasound applications.

In another aspect, the present invention relates to a therapeutic ultrasound kit. The therapeutic ultrasound kit includes at least one low-profile ultrasound transducer and at least one ultrasound coupling device as described herein. The at least one ultrasound coupling device is configured to be operatively coupled to the at least one low-profile ultrasound transducer, thereby forming a transducer/coupling device unit. Various energy generating modules (e.g., portable power devices) can be used to supply electric energy to the at least one low-profile ultrasound transducer, which in turn produces ultrasonic energy for various ultrasound applications.

In another aspect, the present invention relates to a method for performing physiotherapy on a subject. This method involves providing at least one low-profile ultrasound transducer operatively coupled with at least one ultrasound coupling device of the present invention, thereby forming at least one transducer/coupling device unit. The at least one transducer/coupling device unit is used to apply therapeutic ultrasonic energy to a subject, where the therapeutic ultrasonic energy is generated by the at least one low-profile ultrasound transducer.

In another aspect, the present invention relates to a method for applying ultrasonic energy to a subject. This method involves providing at least one low-profile ultrasound transducer operatively coupled with at least one ultrasound coupling device of the present invention, thereby forming at least one transducer/coupling device unit. The at least one transducer/coupling device unit is used to apply therapeutic ultrasonic energy to a subject, where the therapeutic ultrasonic energy is generated by the at least one low-profile ultrasound transducer.

In another aspect, the present invention relates to a method of topically delivering a drug to a subject. This method involves providing at least one low-profile ultrasound transducer operatively coupled with at least one ultrasound coupling device of the present invention, thereby forming at least one transducer/coupling device unit, where the coupling device further contains a deliverable component that includes a drug to be delivered to a subject. The at least one transducer/coupling device unit is used to apply ultrasonic energy to a surface of a subject along with the deliverable component, where the ultrasonic energy is generated by the low-profile ultrasound transducer and emitted through the semi-permeable membrane of the coupling device.

With regard to the various methods of the present invention, the ultrasound coupling device is operative to be used with an ultrasound transducer (e.g., a low-profile ultrasound transducer) that is able to emit ultrasonic energy at a frequency and intensity effective to penetrate deep into the tissue of the subject, and that portable and not limited to just providing surface ultrasonic energy.

The ultrasound coupling device of the present invention is suitable for use with various ultrasound transducer systems. In one particular embodiment, the ultrasound coupling device is effective for use with a low-profile therapeutic ultrasound transducer.

For example, the ultrasound coupling device can be configured as an ultrasound transmission patch and be used as a means of temporarily holding an ultrasound transducer in place, and efficiently acoustically coupling the ultrasound transducer to another object (e.g., a human). In such an embodiment, the patch/coupling device can be similar to an adhesive bandage used to cover a cut; however, it may have an internal pouch that securely holds the transducer in place. Additionally, the pouch in the patch that the transducer is inserted into can have an ultrasound transmission medium (e.g., ultrasound gel), also referred to herein as an ultrasound conductive medium, that acoustically couples the ultrasound transducer from the patch to the body of interest. The patch allows for temporary placement and coupling of ultrasound transducers in a variety of configurations without the direct application of acoustic transmission medium to the body of interest.

In another example, the ultrasound coupling device may be designed in various embodiments to apply acoustic coupling from the transducer to the object (e.g., a human or animal) without the requirement of securing the transducer in one spot.

Therefore, the present invention provides an ultrasound coupling device that is flexible for use with wearable, portable therapeutic ultrasound systems, as well as with standard in-office therapeutic ultrasound systems.

These and other objects, features, and advantages of this invention will become apparent from the following detailed description of the various aspects of the invention taken in conjunction with the accompanying drawings.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, as provided, like reference numerals contained in the drawings are meant to identify similar or identical elements.

FIG. 2A shows the individual components prior to coupling, with low-profile ultrasound transducer 50 having lens portion 71, piezoelectric component 60, and support portion 72. FIG. 2B shows low-profile ultrasound transducer 50 coupled with ultrasound coupling device 100. FIG. 2C shows ultrasound coupling device 100, low-profile ultrasound transducer 50, and ultrasound conductive medium 700 prior to coupling. FIG. 2D shows ultrasound coupling device 100, low-profile ultrasound transducer 50, and ultrasound conductive medium 700 coupled together and in operative placement on surface 111 of subject 110.

FIG. 9A shows the ultrasound coupling device and low-profile ultrasound transducer prior to coupling. FIG. 9B shows the ultrasound coupling device and low-profile ultrasound transducer coupled together to form a single transducer/coupling device unit 600.

FIG. 13A shows the ultrasound apparatus by itself. FIG. 13B shows the ultrasound apparatus as applied to the lower back region of a human subject.

FIGS. 15A and 15B are illustrations of a bandage (FIG. 15A) and wrap (FIG. 15B) that can be used to secure the ultrasound coupling device and a low-profile ultrasound transducer to a subject. FIG. 15C is an illustration showing the application of an ultrasound transducer system (containing a low-profile ultrasound transducer coupled thereto) to the ankle/lower leg region of a horse using a wrap.

FIG. 16A shows the ultrasound coupling device prior to connection of the enabler component to the insert component. FIG. 16B shows the ultrasound coupling device with the enabler component in contact with the insert component. FIG. 16C is a side view showing the enabler component 910/insert component 910b in contact with one another.

DETAILED DESCRIPTION OF THE INVENTION

The present invention relates to an ultrasound coupling device suitable for use with low-profile ultrasound transducers and systems. The ultrasound coupling device of the present invention is particularly suitable for use with portable ultrasound devices, systems, and methods. Further, the ultrasound coupling device of the present invention can be configured to be either disposable or re-useable, and can be used with ultrasound transducers that are either disposable or re-usable. Therefore, in one aspect, the present invention provides an entirely autonomous ultrasound coupling device for use with portable ultrasound transducers and systems. In addition, the ultrasound coupling device of the present invention can be configured so as to enable the generation of ultrasonic energy from an ultrasound transducer or system. In this configuration, the ultrasound coupling device is configured so that ultrasonic energy is only transmitted when the ultrasound transducer is properly coupled with the ultrasound coupling device. For example, as illustrated herein, in various embodiments, the ultrasound coupling device of the present invention provides an enabler component that connects to the transducer to allow the transducer to operate to emit ultrasonic energy. In another embodiment, the ultrasound coupling device can be configured so that the connection between the transducer and energy generating module is completed once the transducer is properly placed within the ultrasound coupling device. In this embodiment, the ultrasound coupling device of the present invention can be designed to custom fit a particular transducer, so that the ultrasound coupling device guides the proper placement of the transducer into the ultrasound coupling device. In another aspect, the ultrasound coupling device of the present invention provides strain relief to wiring or cables that connect to the transducer when coupled with the ultrasound coupling device of the present invention. This enables the ultrasound coupling device to protect the transducer for safe and re-usable uses.

Figure 1:
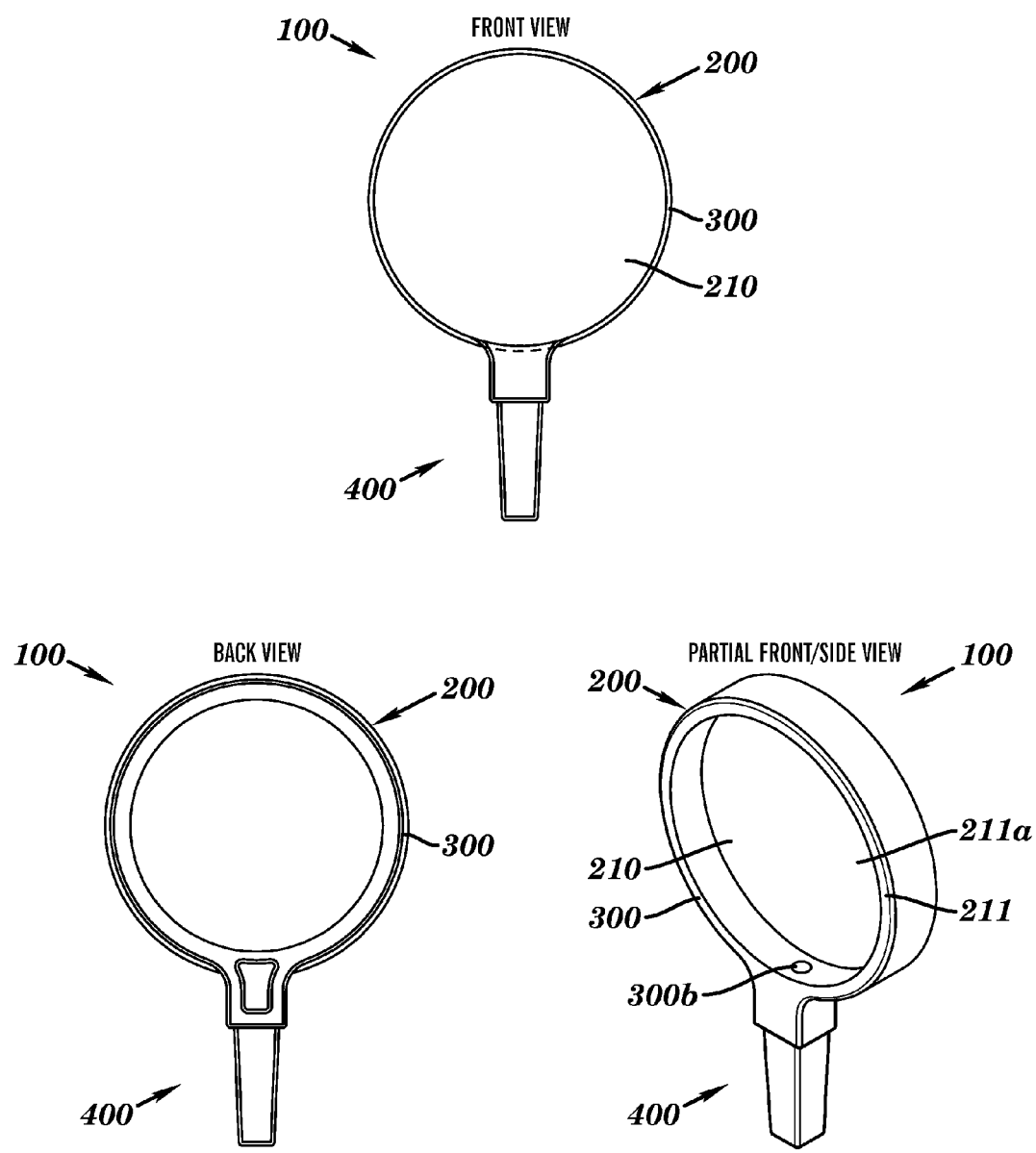
FIG. 1 is an illustration of one embodiment of the ultrasound coupling device of the present invention. The ultrasound coupling device is shown in front view, back view, and partial front/side view perspectives.

As shown in FIG. 1, ultrasound coupling device 100 includes coupling compartment 200. Coupling compartment 200 includes chamber 210 having continuous side wall 300 and opening 211a on first end 211 of chamber 210.

Figure 2A:
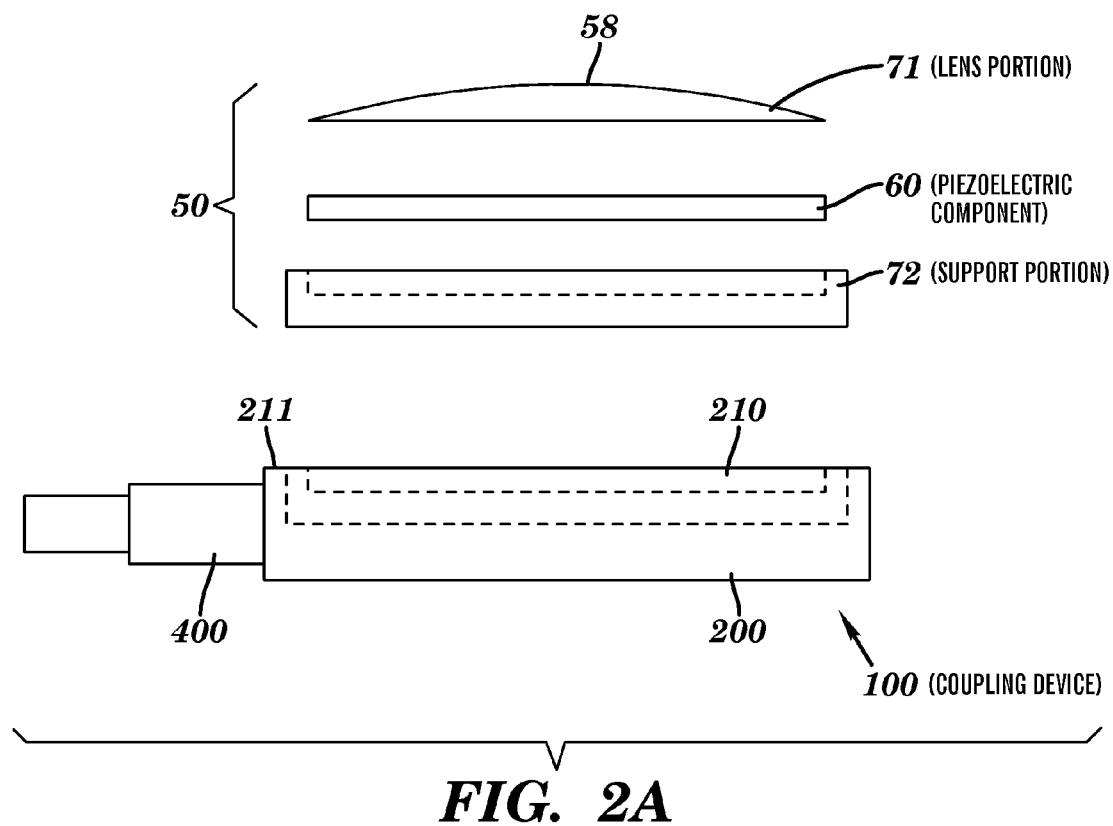
FIGS. 2A-2D are illustrations of an embodiment of the ultrasound coupling device of the present invention coupled with a low-profile ultrasound transducer.
Figure 2B:
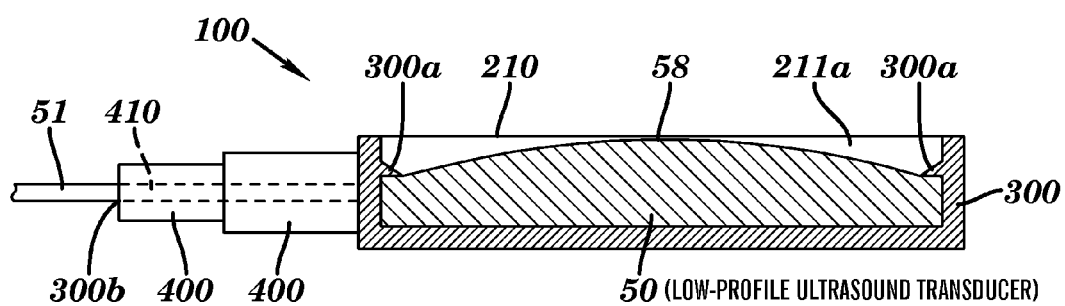
Figure 2C:
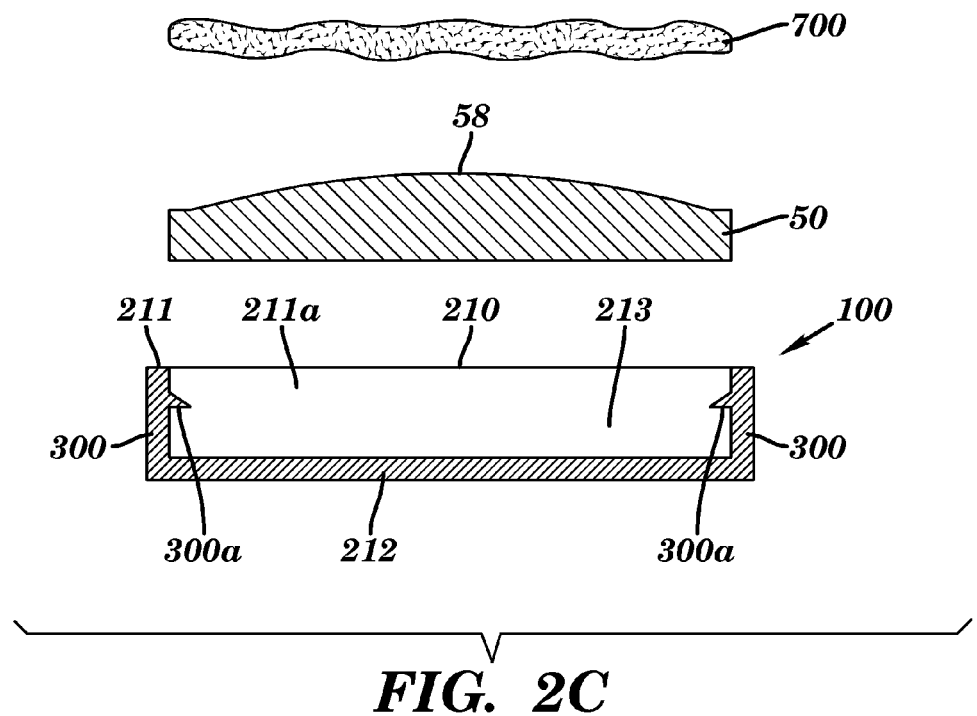
Figure 2D:
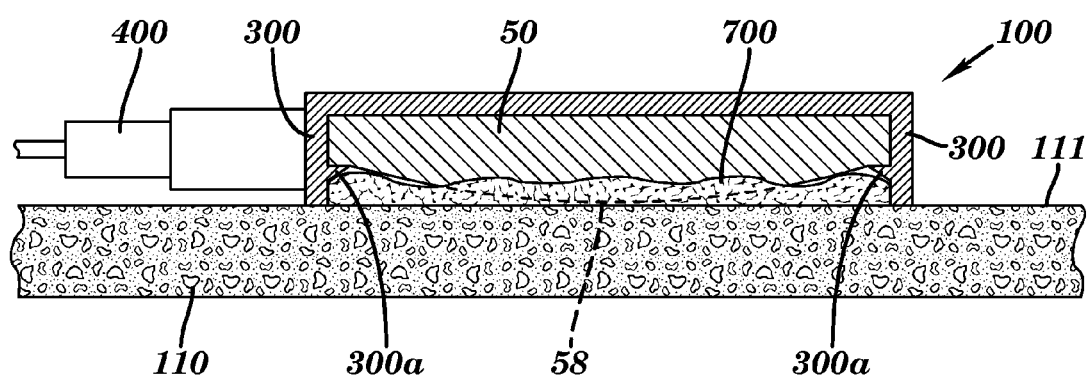

As shown in FIGS. 2A-2D, continuous side wall 300 is configured to hold low-profile ultrasound transducer 50 within chamber 210 so that front ultrasound emitting surface 58 of low-profile ultrasound transducer 50 faces outward toward opening 211a of chamber 210. Front ultrasound emitting surface 58 is configured to control the direction and wave pattern of ultrasonic energy emitted from low-profile ultrasound transducer 50. As shown in FIGS. 2B-2D, continuous side wall 300 is also configured to hold a quantity of ultrasound conductive medium 700 within chamber 210 and operative to keep ultrasound conductive medium 700 in simultaneously contact with surface 111 of subject 110 and with at least a portion of front ultrasound emitting surface 58 of low-profile ultrasound transducer 50. For example, as shown in FIGS. 2B-2D, continuous side wall 300 can be configured to include lip portion 300a. In one embodiment, as shown in FIGS. 2B-2D, lip portion 300a is formed on the inner surface of continuous side wall 300 at a position operative to keep low-profile ultrasound transducer 50 in place within chamber 210.

As shown in FIGS. 2C-2D, chamber 210 has a second end 212 opposite to the first end 211. Second end 212 provides a barrier effective to form cavity region 213 within chamber 210, so as to assist in keeping low-profile ultrasound transducer 50 securely in place within cavity region 213/chamber 210.

Figure 3:
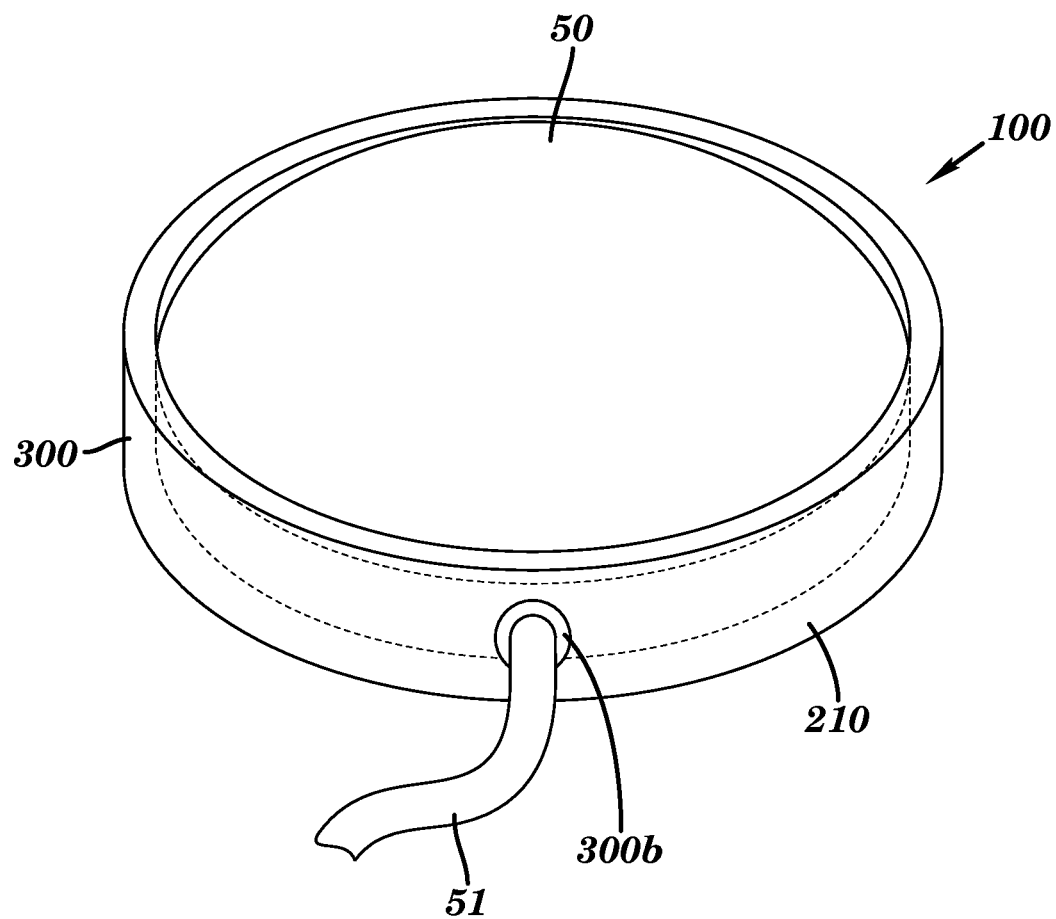
FIG. 3 is an illustration of one embodiment of the ultrasound coupling device of the present invention coupled with a low-profile ultrasound transducer, with ultrasound coupling device 100 having opening 300b for passable of cable 51.

As shown in FIG. 3, in one embodiment, continuous side wall 300 can further include opening 300b that is configured to allow cable 51, which is connected to low-profile ultrasound transducer 50 to extend outside of chamber 210. As shown in FIG. 2B, in another embodiment, opening 300b can be configured as cable support extension 400 that extends outward from continuous side wall 300 and includes passage way 410 for cable 51.

Figure 4:
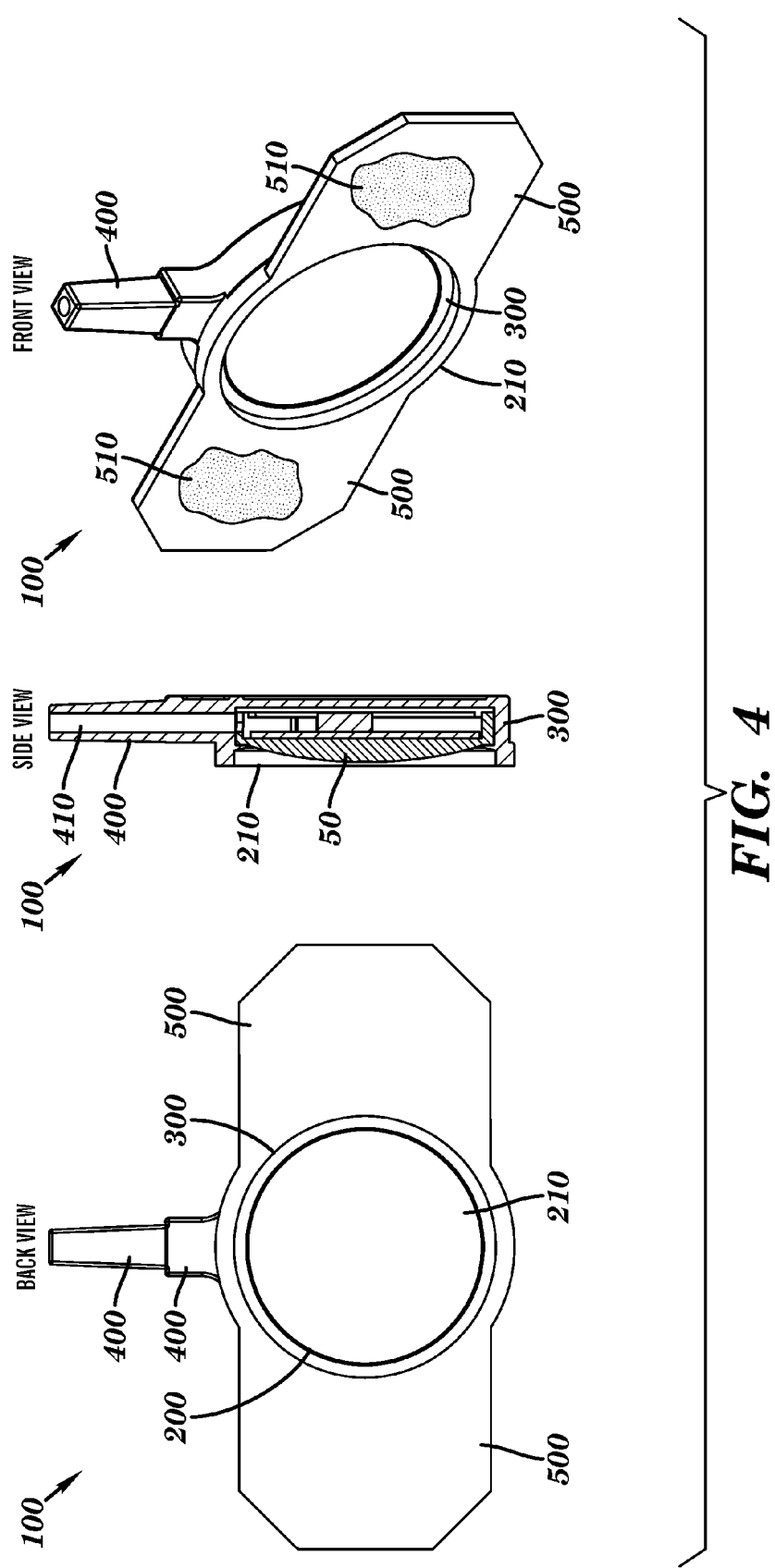
FIG. 4 provides perspective views of one embodiment of the ultrasound coupling device of the present invention. The ultrasound coupling device is shown in front view, back view, and side view perspectives.
Figure 5:
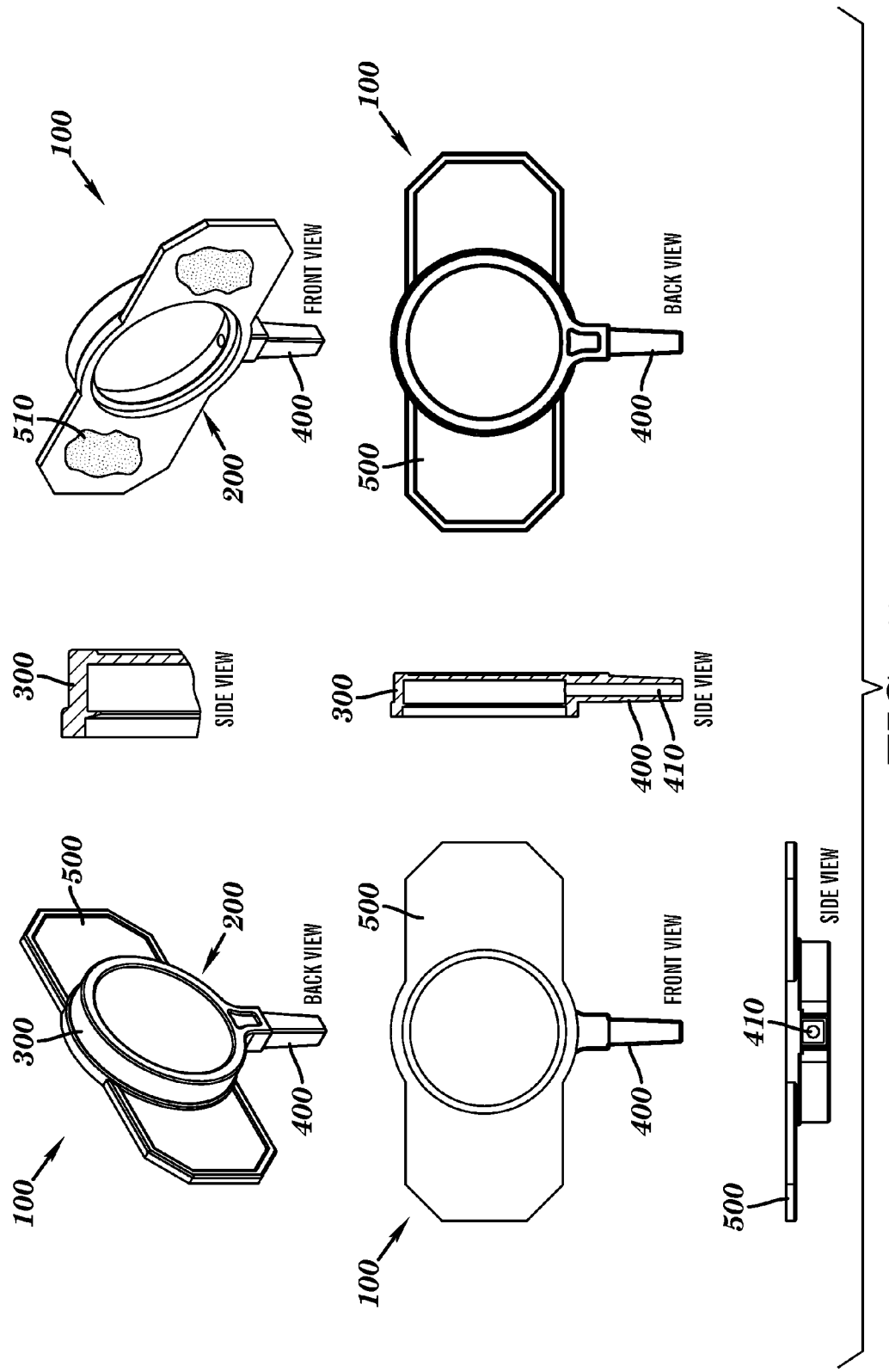
FIG. 5 provides perspective views of one embodiment of the ultrasound coupling device of the present invention. The ultrasound coupling device is shown in two front view, two back view, and three side view perspectives. For illustrative purposes, dimensions of this particular embodiment of the ultrasound coupling device are shown, but are not meant to limit the ultrasound coupling device of the present invention to particular dimensions.
Figure 6:
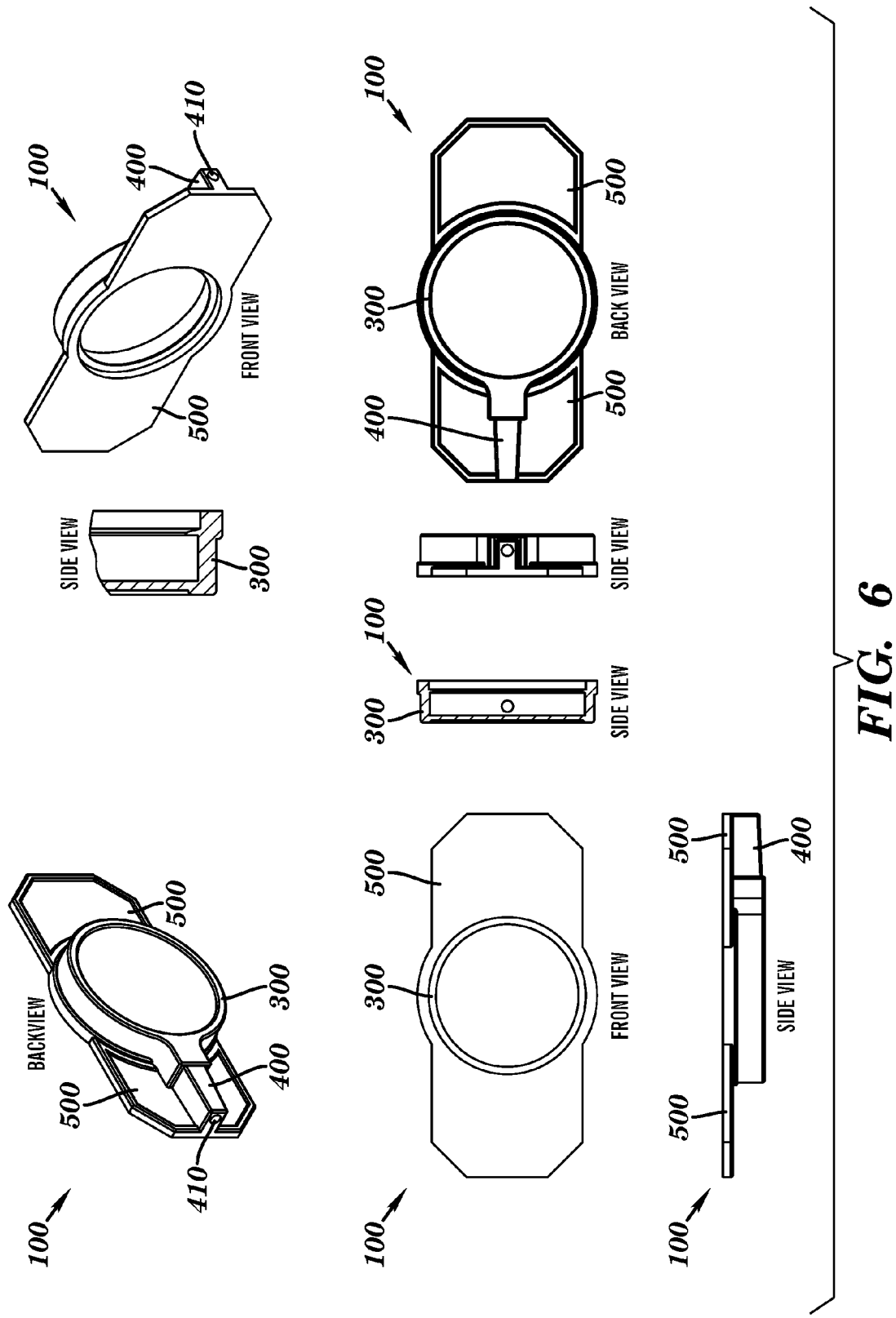
FIG. 6 provides perspective views of one embodiment of the ultrasound coupling device of the present invention. The ultrasound coupling device is shown in two front view, two back view, and four side view perspectives. For illustrative purposes, dimensions of this particular embodiment of the ultrasound coupling device are shown, but are not meant to limit the ultrasound coupling device of the present invention to particular dimensions.

As shown in FIGS. 4-6, coupling compartment 200 can further include flange region 500 extending outward from at least a portion of continuous side wall 300 of chamber 210. Flange region 500 can be made of various types of materials, including materials that are non-adhesive or adhesive. The term "adhesive" is meant to include any material operative to removeably secure ultrasound coupling device 100 to surface 111 of subject 110. For example, suitable adhesives can include glue or glue-like materials (e.g., used with disposable bandages) suitable for use with humans or animals, as well as materials such as Velcro attachments and materials that are held in place mechanically. Thus, the present invention contemplates at least a portion of flange region 500 to include adhesive material 510 effective to keep ultrasound coupling device 100 in place on surface 111 of subject 110.

FIG. 4 shows an embodiment of ultrasound coupling device 100 having flange region 500 extending on opposite sides of continuous side wall 300, with cable support extension 400 extending in a direction about 90 degrees from flange regions 500. FIG. 4 shows a front view, a back view, and a side view perspective of this embodiment of ultrasound coupling device 100. In the side view of FIG. 4, low-profile ultrasound transducer 50 is shown disposed in chamber 210 of ultrasound coupling device 100, with low-profile ultrasound transducer 50 not extending above continuous side wall 300. Other embodiments of the present invention also include low-profile ultrasound transducer 50 extending above continuous side wall 300. In the front view of FIG. 4, adhesive material 510 is shown deposited on portions of flange regions 500. Other embodiments of the present invention include adhesive material 510 being deposited on flange region 500 at other locations and/or on part of continuous side wall 300 at opening 211a of chamber 210, in a manner sufficient to assist in securing ultrasound coupling device 100/low-profile ultrasound transducer 50 in place on the surface of a subject. As with all embodiments, flange regions 500 can be made of a flexible material in order to enable it to mold to the surface of a subject (e.g., around a wrist or knee area). Silicone is one example of a suitable material for flange regions 500 and ultrasound coupling device 100.

FIG. 5 is similar to the embodiment in FIG. 4, in that it shows an embodiment of ultrasound coupling device 100 having flange region 500 extending on opposite sides of continuous side wall 300, with cable support extension 400 extending in a direction about 90 degrees from flange regions 500. FIG. 5 shows perspectives of two front views, two back views, and three side views of this embodiment of ultrasound coupling device 100. A magnified side view of a portion of continuous side wall 300 is shown. Also, additional side views show passage way 410 of cable support extension 400.

FIG. 6 shows an embodiment of ultrasound coupling device 100 having flange region 500 extending on opposite sides of continuous side wall 300, with cable support extension 400 extending along one of the flange regions 500. FIG. 6 shows perspectives of two front views, two back views, and four side views of this embodiment of ultrasound coupling device 100.

Figure 7:
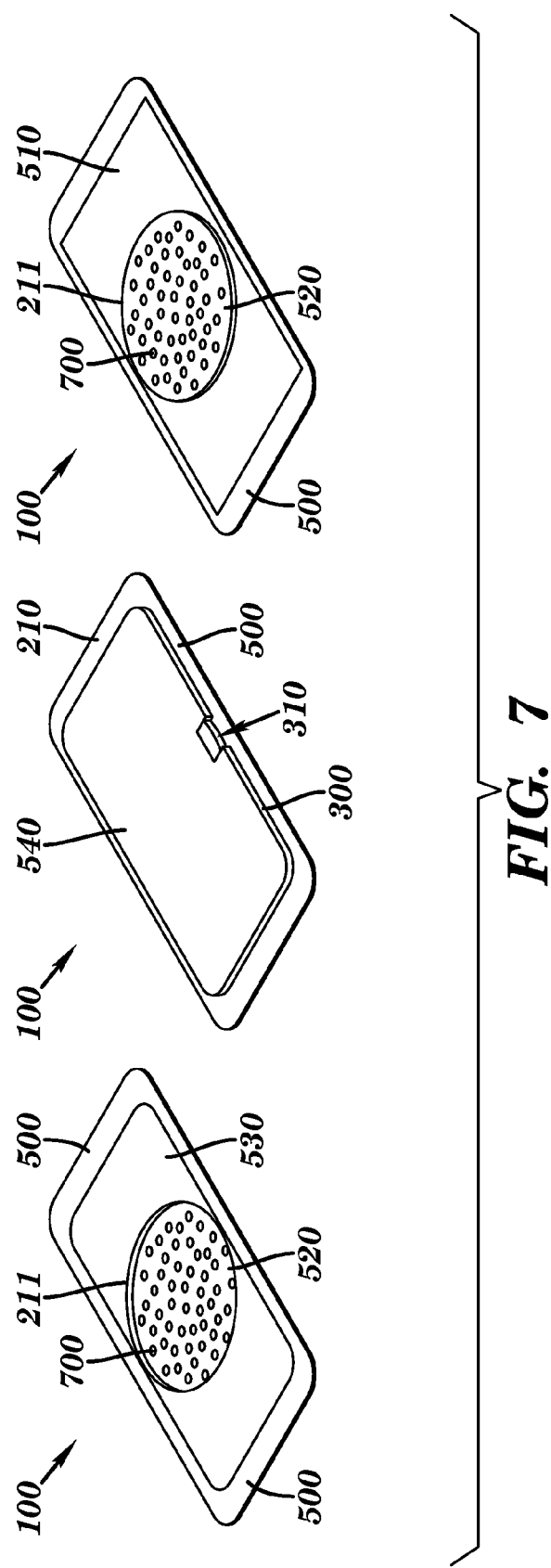
FIG. 7 is an illustration of various perspectives of one embodiment of the ultrasound coupling device of the present invention. This embodiment includes a semi-permeable membrane for passage of an ultrasound conductive medium or deliverable component therethrough.
Figure 8:
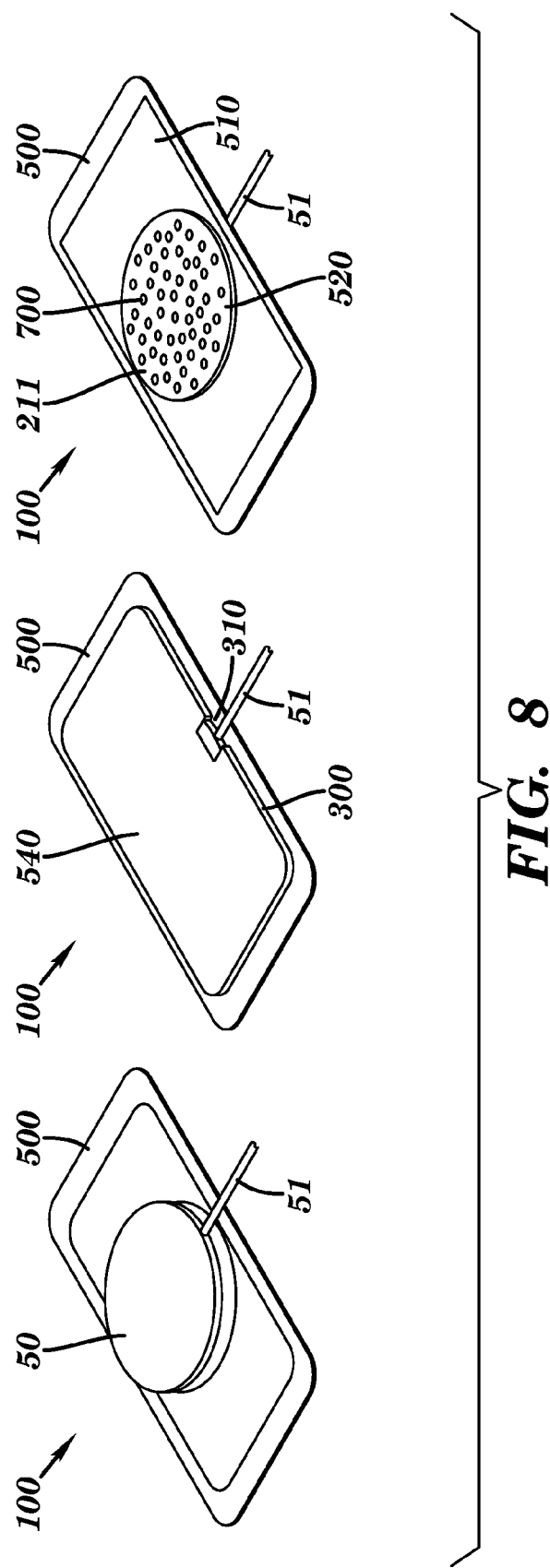
FIG. 8 is an illustration of various perspectives of one embodiment of the ultrasound coupling device of the present invention. This embodiment includes a semi-permeable membrane for passage of an ultrasound conductive medium or deliverable component therethrough. Also shown is the ultrasound coupling device coupled with a low-profile ultrasound transducer.

As shown in FIGS. 7-8, in one embodiment, ultrasound coupling device 100 can further include semi-permeable membrane 520 configured to cover opening 211a of first end 211 of chamber 210. Semi-permeable membrane 520 is effective to allow ultrasound conductive medium 700 to be released from first end 211 of coupling compartment 200 when pressure is applied to semi-permeable membrane 520. Pressure to semi-permeable membrane 520 can be applied by the subject manually by pressing down on ultrasound coupling device 100, or the pressure can be applied by a garment type of apparatus (e.g., a holder component such as a Neoprene wrap) holding ultrasound coupling device 100 against surface 111 of subject 110.

Ultrasound conductive medium 700 can include any material that is effective as a conductor of ultrasound energy from low-profile ultrasound transducer 50 to surface 111 of subject 110. Examples of a suitable ultrasound conductive medium 700 include, without limitation, a gel, a hydrogel, an acoustic gel, saline, a low-viscosity liquid, and the like.

As shown in FIGS. 7-8, in one embodiment, ultrasound coupling device 100 can further include covering sheet 530 attached to flange region 500 and configured to cover semi-permeable membrane 520. Covering sheet 530 can be configured to be manually removable from flange region 500 in order to expose semi-permeable membrane 520 when the subject is ready to use ultrasound coupling device 100. Semi-permeable membrane 520 can also be configured to be optically transparent and/or translucent, thereby allowing light emitted from low-profile ultrasound transducer 50 to penetrate through semi-permeable membrane 520. Backing panel 540 can also be used to keep low-profile ultrasound transducer 50 in place, and can be configured to be removeable to enable the removal of low-profile ultrasound transducer 50. Backing panel 540 can also be applied after low-profile ultrasound transducer 50 is placed within chamber 210.

As shown in FIGS. 7-8, in one embodiment, ultrasound coupling device 100 can be configured so that at least a portion 310 of continuous side wall 300 of chamber 210 is configured to allow low-profile ultrasound transducer 50 to be inserted into chamber 210 through portion 310, rather than through first end 211 or second end 212 of chamber 210.

Figure 9A:
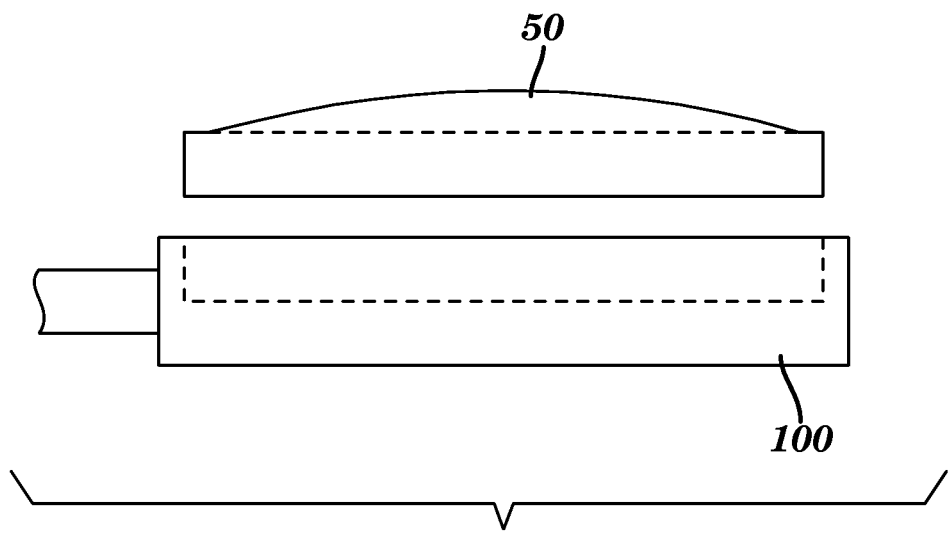
FIGS. 9A-9B are illustrations of one embodiment of the ultrasound coupling device of the present invention and a suitable low-profile ultrasound transducer for use with the ultrasound coupling device.
Figure 9B:
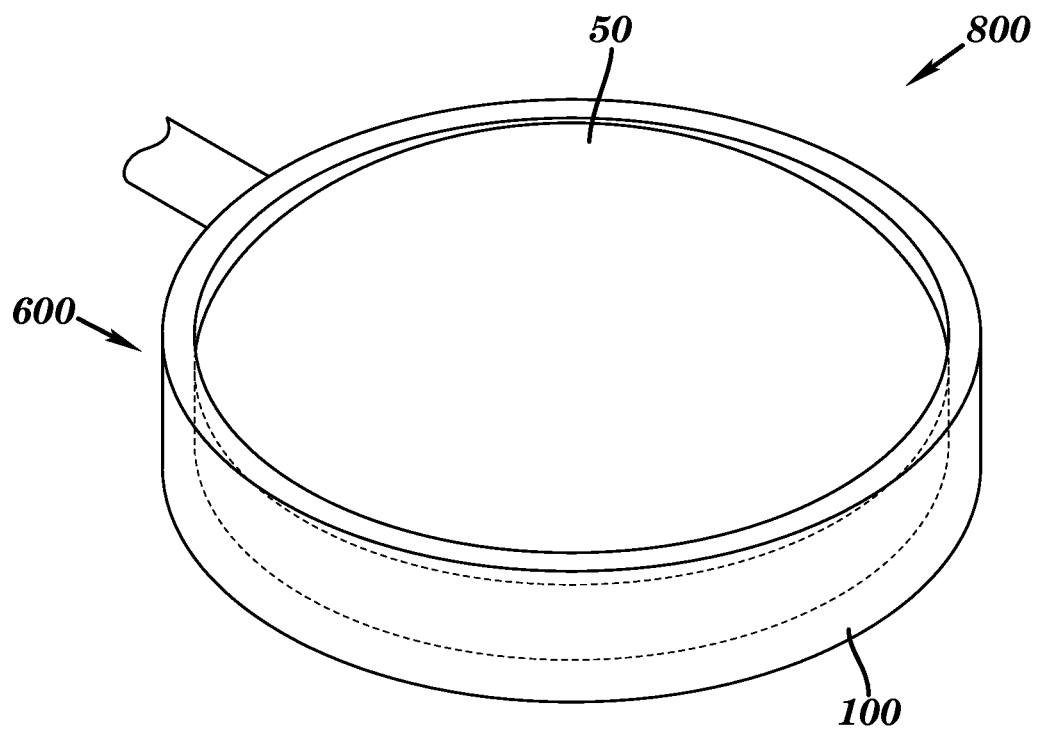

The present invention also relates to an ultrasound apparatus that includes at least one low-profile ultrasound transducer and at least one ultrasound coupling device as disclosed herein. As shown in FIGS. 9A-9B, ultrasound apparatus 800 includes at least one ultrasound coupling device 100 operatively coupled to at least one low-profile ultrasound transducer 50, thereby forming transducer/coupling device unit 600. Any of the low-profile ultrasound transducers and any of the ultrasound coupling devices described herein are suitable to be combined into transducer/coupling device unit 600. FIG. 9A shows low-profile ultrasound transducer 50 and ultrasound coupling device 100 as individual components, prior to being combined. FIG. 9B shows low-profile ultrasound transducer 50 and ultrasound coupling device 100 combined into transducer/coupling device unit 600.

As shown in FIGS. 10-15, in various embodiments, ultrasound apparatus 800 can further include holder component 900, which is configured to hold transducer/coupling device unit 600 in place on or in operative proximity to surface 111 of subject 110. As shown in the illustrative examples of FIGS. 10-15, holder component 900 can be configured to hold one or more transducer/coupling device units 600. Suitable holder components 900 can include any wearable apparatus, including, for example, clothing (see FIG. 14), wraps (see FIGS. 10, 11, 12, 13A, and 13B) such as Neoprene wraps and other athletic wraps (see FIGS. 15A-15C) well known in the art (e.g., ACE bandages and the like), with the wearable apparatus being designed to hold one or more transducer/coupling device units 600. Thus, ultrasound apparatus 800 can be used for applying ultrasonic energy or therapy to human and animal subjects at any location, including without limitation, the following areas ankles, elbows, knees, wrists, hands, feet, arms, fingers, thighs, back area, neck, etc.

Figure 10:
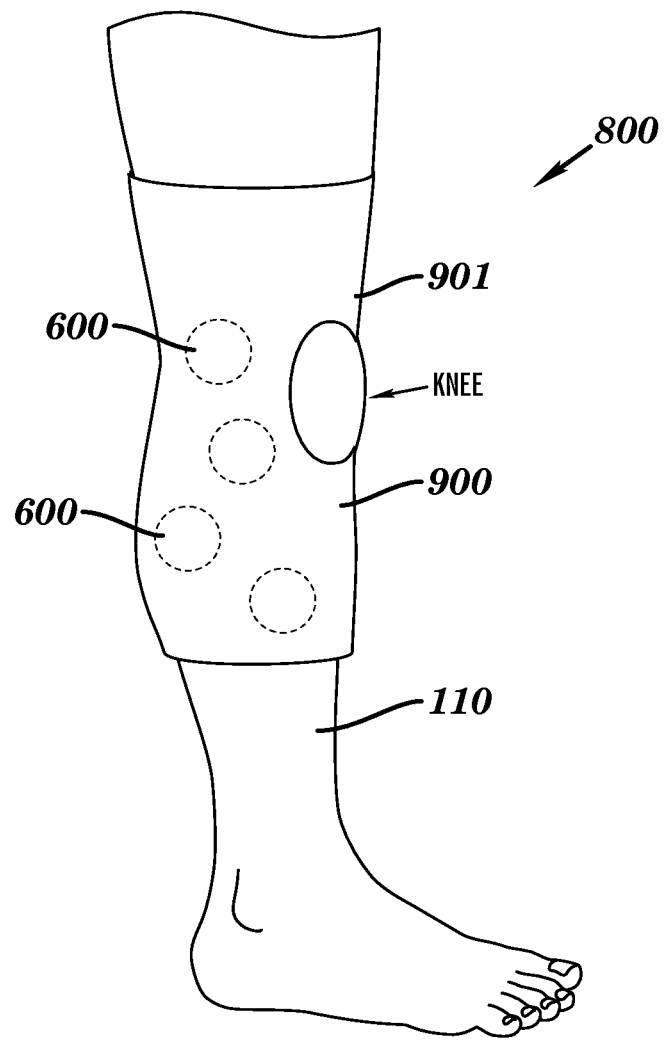
FIG. 10 illustrates one embodiment of the ultrasound apparatus of the present invention. The ultrasound apparatus is configured for use at and around the knee of a human subject.

FIG. 10 shows an embodiment of ultrasound apparatus 800 having holder component 900 configured as a multi-unit holder component 902 for use on and around the knee area of a human subject. Other similar embodiments can include a single-unit holder component 901.

Figure 11:
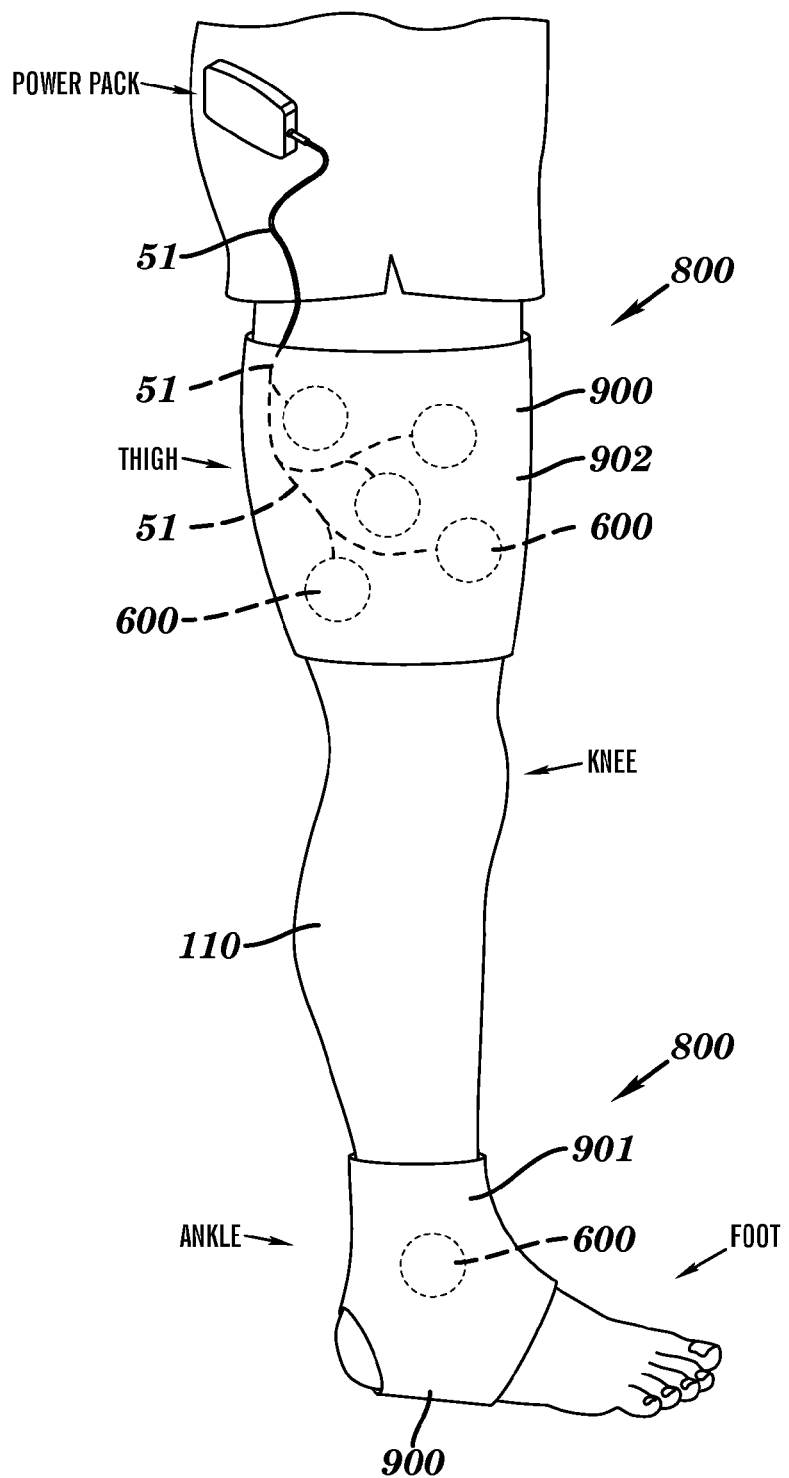
FIG. 11 illustrates two embodiments of the ultrasound apparatus of the present invention. One embodiment shows the ultrasound apparatus configured for use at and around the ankle and foot region of a human subject. The other embodiment shows the ultrasound apparatus configured for use at and around the thigh region of a human subject.

FIG. 11 shows two embodiments of ultrasound apparatus 800. One embodiment has holder component 900 configured as a multi-unit holder component 902 for use on and around the thigh area of a human subject. This embodiment also illustrates the use of a separate power pack (e.g., battery pack and/or energy generating module as described herein), showing cable 51 connected to the plurality of transducer/ coupling device units 600. Cable 51 is shown in just one configuration, but any other operative configurations of cable 51 connections are covered by the present invention. Another embodiment of ultrasound apparatus 800 shown in FIG. 11 illustrates holder component 900 configured as a single-unit holder component 901 for use on and around the ankle and foot area of a human subject.

Figure 12:
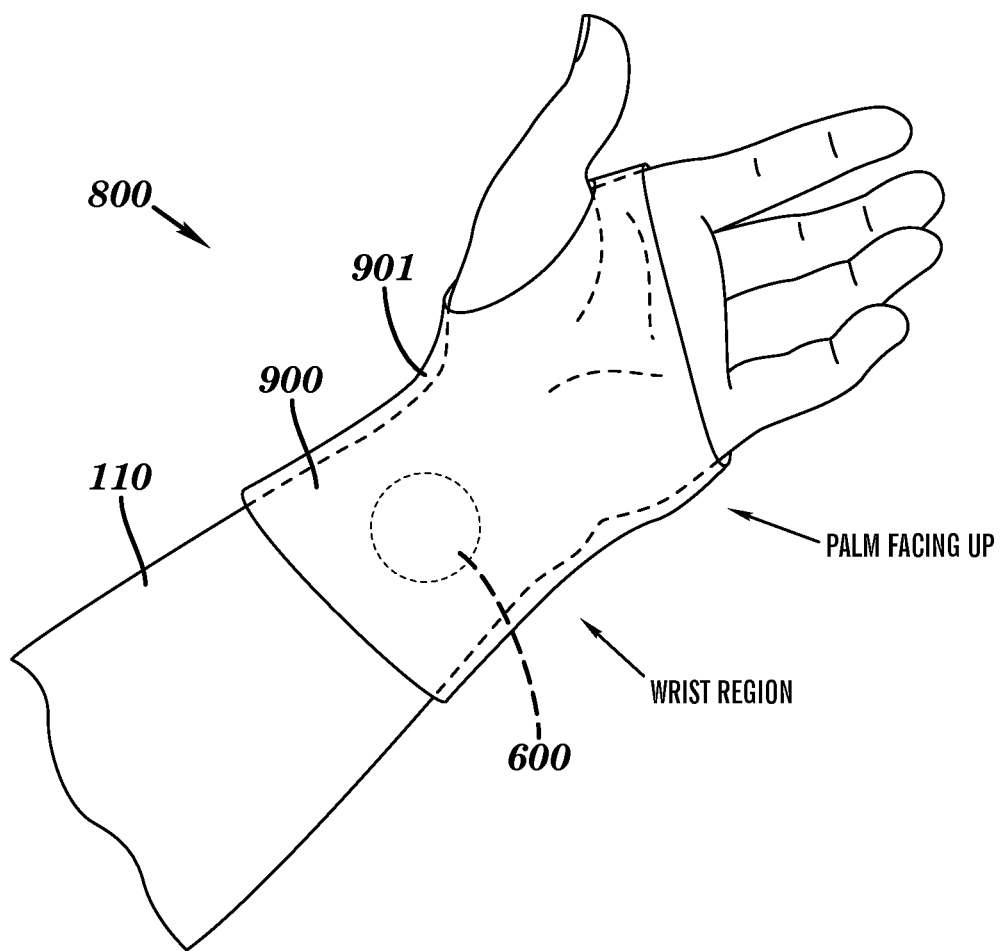
FIG. 12 illustrates one embodiment of the ultrasound apparatus of the present invention. The ultrasound apparatus is configured for use at and around the wrist and hand region of a human subject.

FIG. 12 shows an embodiment of ultrasound apparatus 800 having holder component 900 configured as a single-unit holder component 901 for use on and around the wrist and hand area of a human subject. Other similar embodiments can include a multi-unit holder component 902.

Figure 13A:
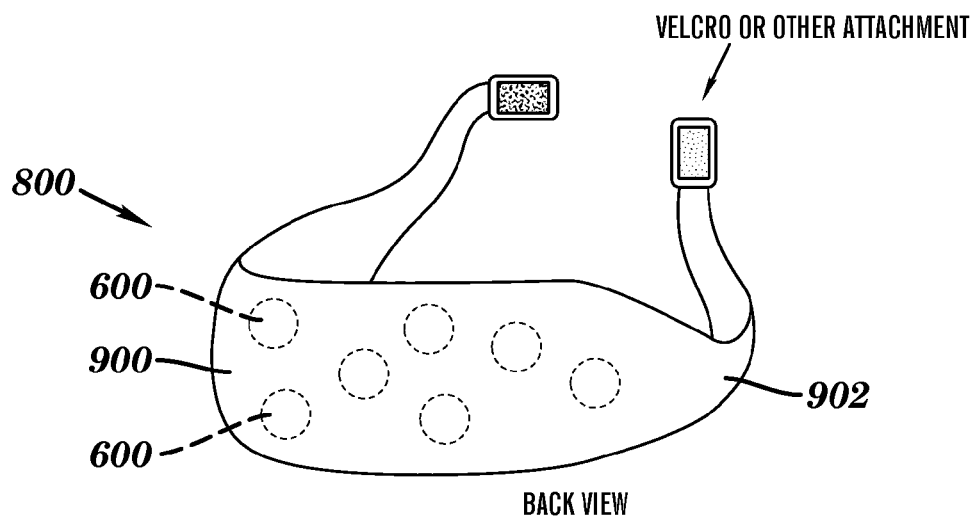
FIGS. 13A-13B illustrate one embodiment of the ultrasound apparatus of the present invention. The ultrasound apparatus is configured for use at and around the lower back region of a human subject.
Figure 13B:
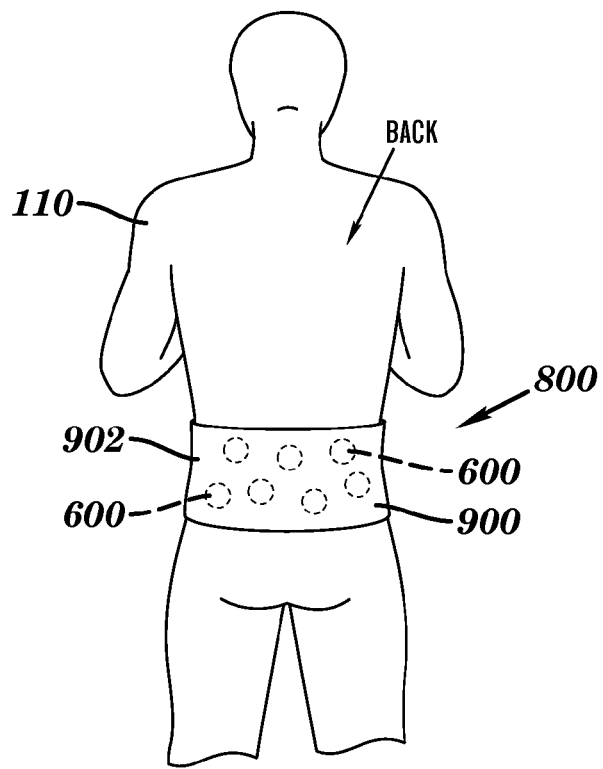

FIGS. 13A-13B show an embodiment of ultrasound apparatus 800 having holder component 900 configured as a multi-unit holder component 902 for use on and around the lower back area of a human subject. For application around the torso, ultrasound apparatus 800 can include attachments on the ends (e.g., Velcro or other types of attachments well known in the art). Multi-unit holder component 902 configurations are particularly useful for treating large areas (e.g., the lower back) of subjects. Other similar embodiments can include a single-unit holder component 901.

Figure 14:
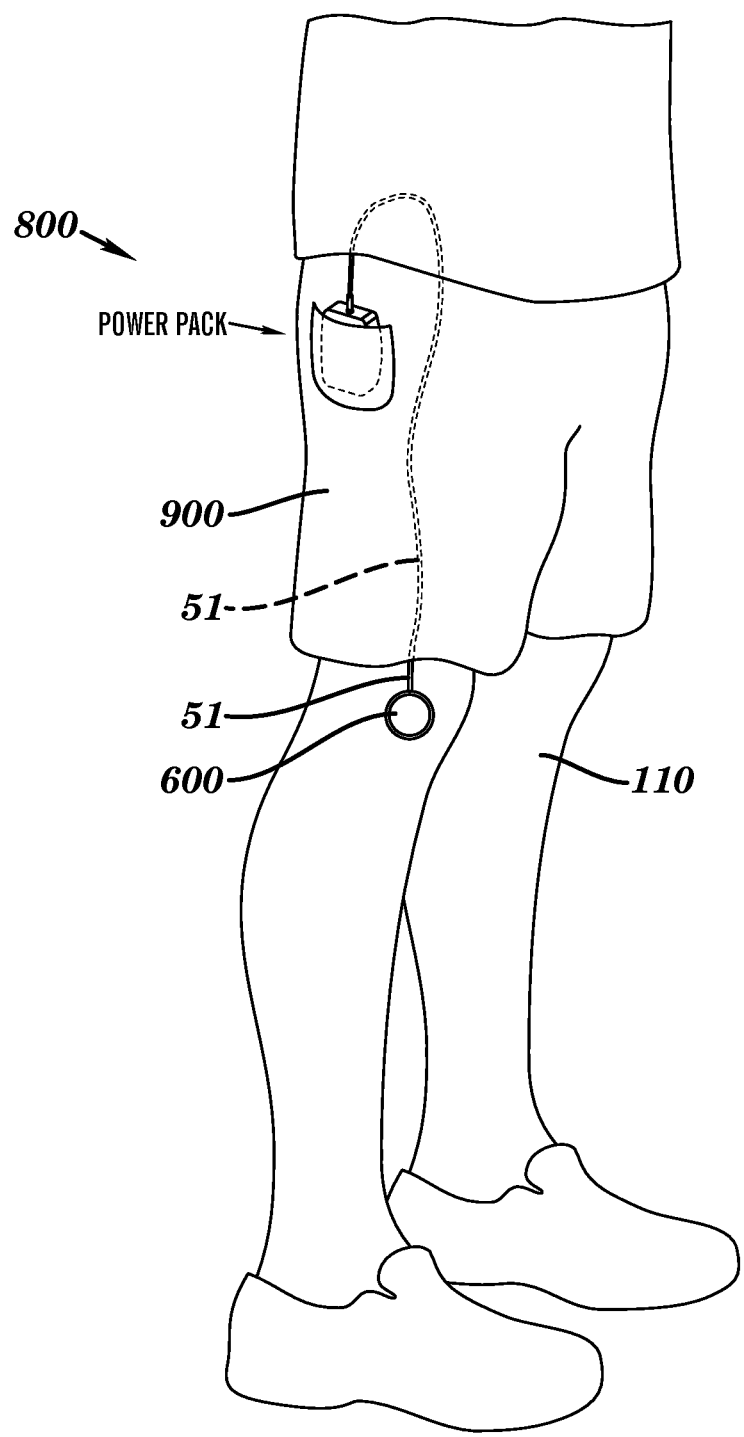
FIG. 14 illustrates one embodiment of the ultrasound coupling device of the present invention as applied to the knee region of a human subject. The ultrasound coupling device is used in tandem with a garment worn by the subject, thereby combining to form one embodiment of the ultrasound apparatus of the present invention.

FIG. 14 shows an embodiment of ultrasound apparatus 800 having holder component 900 configured as a single-unit holder component 901, with a garment (e.g., shorts) being used to hold a portion of an ultrasound system (e.g., a power pack/energy generating module connected by cable 51 to transducer/coupling device unit 600). As shown in FIG. 14, in one embodiment, transducer/coupling device unit 600 is configured so that it attaches to the target area of the subject using an adhesive (e.g., hydrogel or other biocompatible adhesive). Other embodiments can include flange regions 500 to assist in surface attachment to the subject. In FIG. 14, cable 51 can run inside of the garment (or outside), and the power pack/energy generating module can be held in the hand, place on a holding surface, or deposited or attached to the garment (e.g., in a pocket). The garment can also be custom made to hold ultrasound apparatus 800. Other similar embodiments can include a multi-unit holder component 902.

Figure 15A:
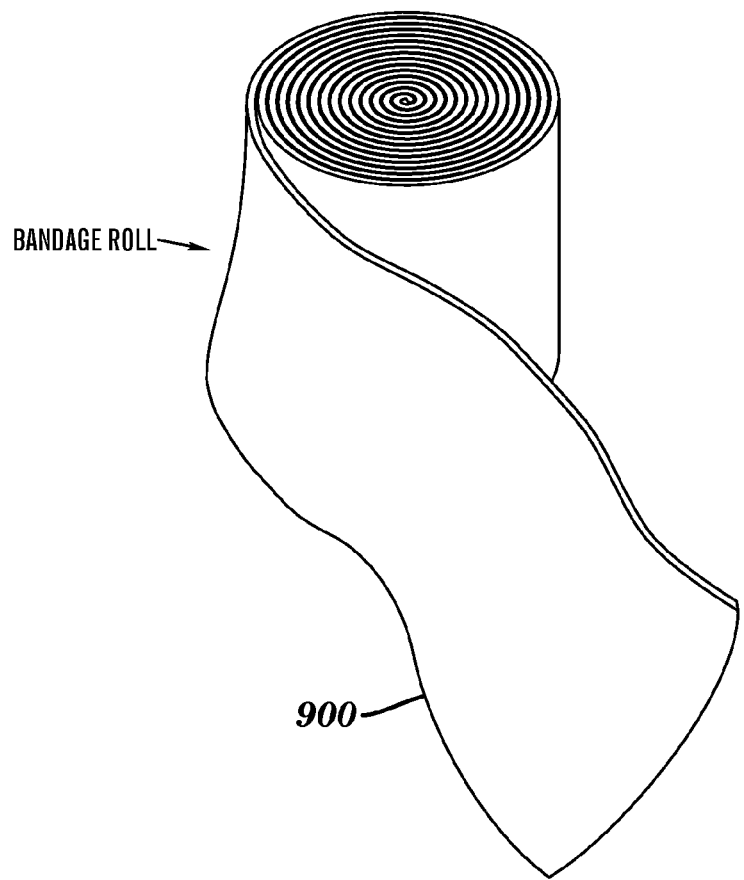
FIGS. 15A-15C illustrate various aspects of embodiments of the ultrasound apparatus of the present invention.
Figure 15B:
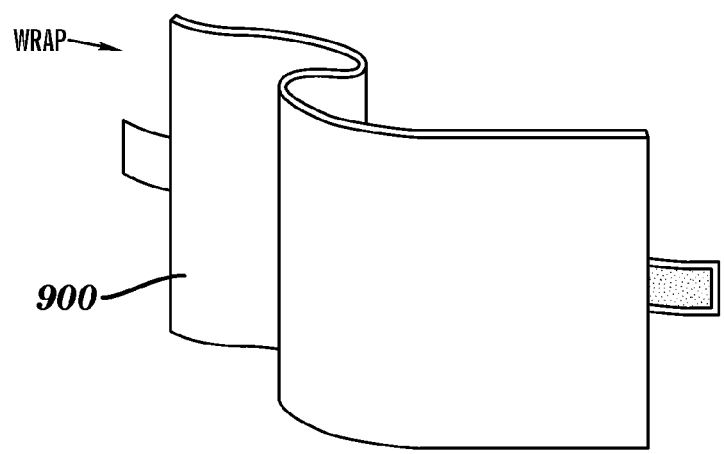
Figure 15C:
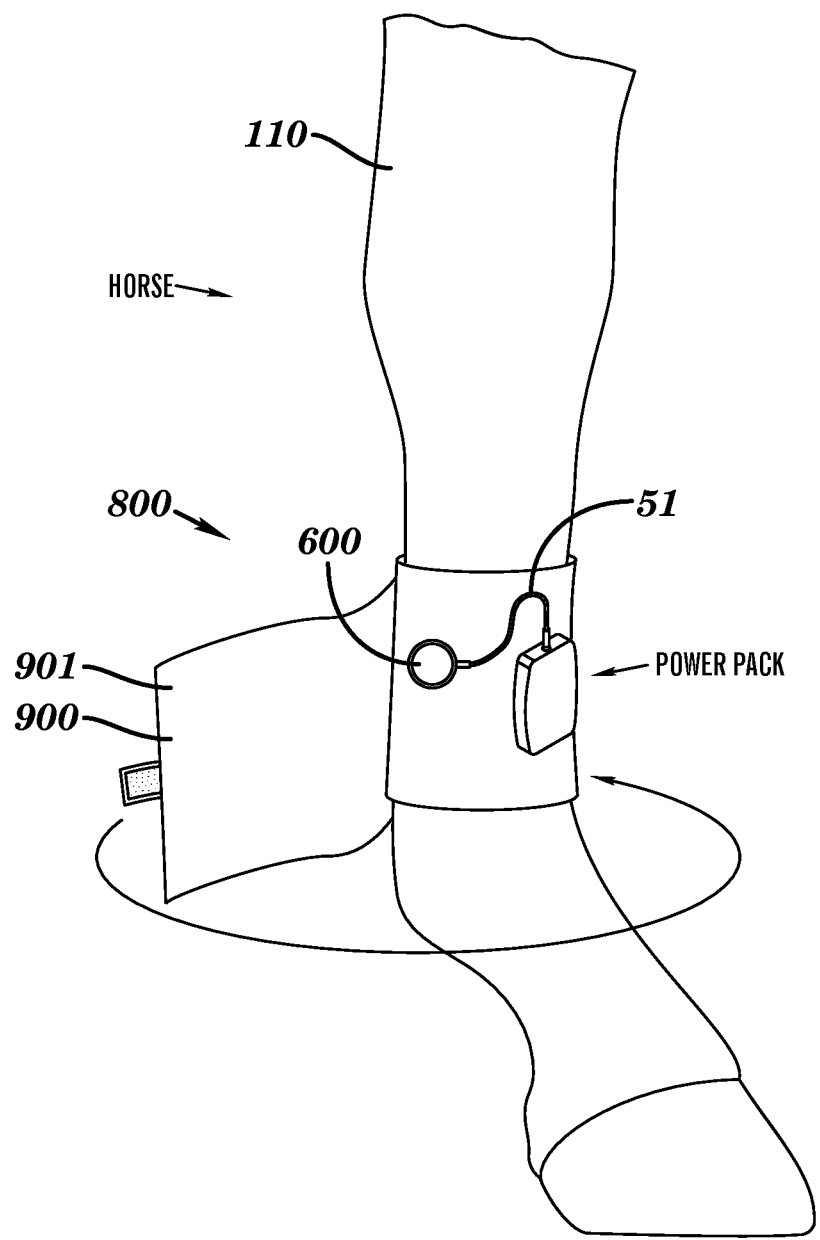

FIGS. 15A-15C show an embodiment of ultrasound apparatus 800 having holder component 900 configured as a single-unit holder component 901 for use on and around the lower leg/ankle region of an animal subject (i.e, a horse as shown). For the embodiment shown, off-the-shelf bandages (e.g., ACE bandages) (FIG. 15A) and wraps (e.g., having end attachments) (FIG. 15B) can be used to secure transducer/coupling device unit 600 in place at or near the target region of the subject. This configuration is particularly useful for animal subjects, where securing the transducer/coupling device unit or units 600 for longer periods of time is important, particularly since the animal subject will not be able to adjust the ultrasound apparatus 800 as would a human subject. As shown in FIG. 15C, in this embodiment, ultrasound apparatus 800 is similar to the one described above for FIG. 14. In FIG. 15C, ultrasound apparatus 800 can be held in place by wrapping holder component 900 around both ultrasound apparatus 800 and the ankle/leg of the horse, and then securely attached for treatment.

All applications using ultrasound apparatus 800 in its various configurations of holder component 900 can be used for both humans and animals. Thus, the figures provided herein with respect to the application of ultrasound apparatus 800 are not meant to be limiting to the subject or area shown.

Figure 16A:
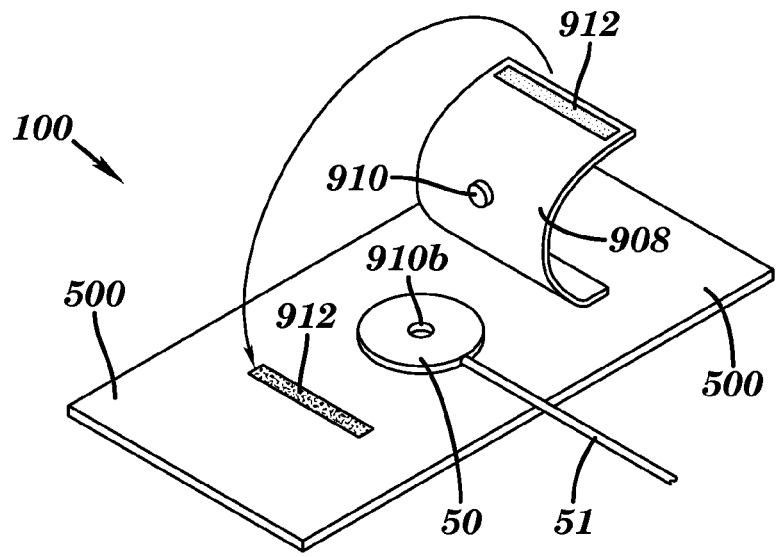
FIGS. 16A-16C are illustrations of one embodiment of the ultrasound coupling device of the present invention. This embodiment includes enabler strap 908 having enabler component 910 (e.g., shaped like a nipple) that fits into insert component 910b of low-profile ultrasound transducer 50 to enable the generation of ultrasonic energy from the low-profile ultrasound transducer 50.
Figure 16B:
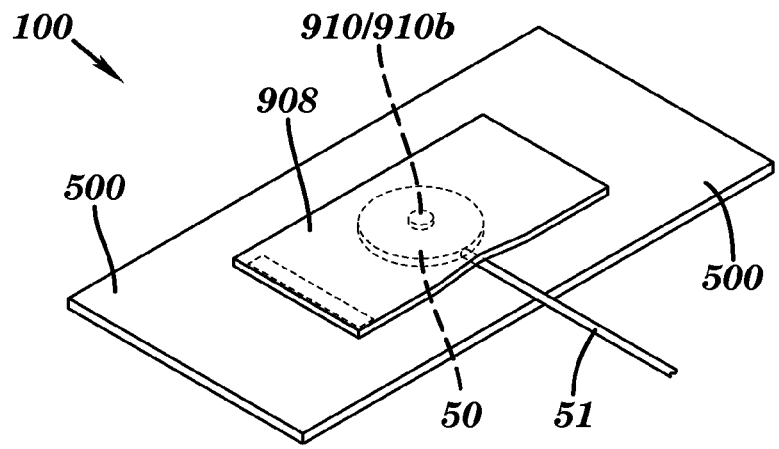
Figure 16C:
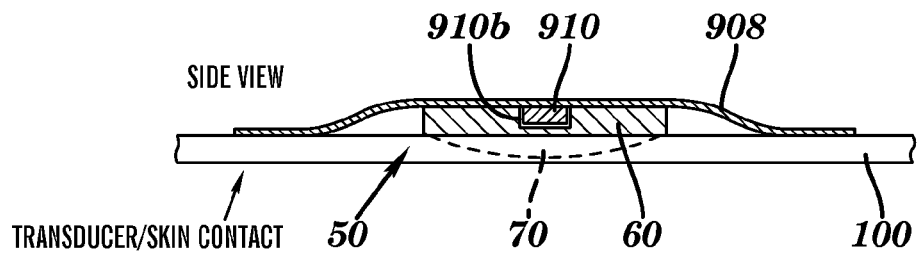

As shown in FIGS. 16A-16C, the ultrasound coupling device of the present invention can be configured with an enabler mechanism, which is used to control the operation of the ultrasound transducer. FIGS. 16A-16C show ultrasound coupling device 100 having enabler strap 908, which includes enabler component 910 (e.g., a metal nipple or metal nipple-like shape). The back portion of low-profile ultrasound transducer 50 includes insert component 910b, which is configured to operatively receive enabler component 910. When enabler 910 component is contacted with insert component 910b, low-profile ultrasound transducer 50 can operate to generate ultrasonic energy, but no such ultrasonic energy is generated when these component are not in contact. To begin generating ultrasonic energy, the user would manipulate enabler strap 908 over low-profile ultrasound transducer 50 to contact enabler component 910 to insert component 910b. Attachments 912 can be used to secure enabler strap 908 in place, with one attachment 912 being on enabler strap 908 and the other attachment 912 on a region of ultrasound coupling device such as a flange region 500.

FIGS. 16A-16C illustrate just one such embodiment of an enabler mechanism, but any configuration that generally operates as shown and described is covered by the present invention.

The present invention also relates to a therapeutic ultrasound kit that includes at least one low-profile ultrasound transducer and at least one ultrasound coupling device as described herein. The at least one ultrasound coupling device is configured to be operatively coupled to the at least one low-profile ultrasound transducer, thereby forming a transducer/coupling device unit. The kit can further include at least one holder component operative to hold the at least one ultrasound coupling device in place on a surface of a subject, where the at least one ultrasound coupling device is operatively coupled to the at least one low-profile ultrasound transducer. The at least one holder component can be configured to hold one or more transducer/coupling device units in place on the surface of the subject.

The present invention also relates to a method for performing physiotherapy on a subject. This method involves the following steps: (i) providing at least one low-profile ultrasound transducer operatively coupled with at least one ultrasound coupling device of the present invention, thereby forming at least one transducer/coupling device unit; and (ii) applying therapeutic ultrasonic energy to a subject, where the therapeutic ultrasonic energy is generated by the at least one low-profile ultrasound transducer.

The present invention also relates to a method for applying ultrasonic energy to a subject. This method involves the following steps: (i) providing at least one low-profile ultrasound transducer operatively coupled with at least one ultrasound coupling device of the present invention, thereby forming at least one transducer/coupling device unit; and (ii) applying ultrasonic energy to a surface of a subject, where the ultrasonic energy is generated by the at least one low-profile ultrasound transducer. This method is operative so that applying the ultrasonic energy to the surface of the subject is effective to alleviate pain in tissue of the subject in and around the surface.

The present invention also relates to a method of topically delivering a drug to a subject. This method involves the following steps: (i) providing at least one low-profile ultrasound transducer (having a semi-permeable membrane as described herein) operatively coupled with at least one ultrasound coupling device as described herein, thereby forming at least one transducer/coupling device unit, where the coupling device further contains a deliverable component that includes a drug to be delivered to a subject; and (ii)

applying ultrasonic energy to a surface of a subject along with the deliverable component, where the ultrasonic energy is generated by the low-profile ultrasound transducer and emitted through the semi-permeable membrane of the coupling device.

The various methods of using the coupling device of the present invention can involve the use of at least one transducer/coupling device held in place on the surface of the subject by an at least one holder component, with the at least one holder component being configured to hold the at least one transducer/coupling device unit in place on the surface of the subject. The holder component can be configured to hold one or more transducer/coupling device units.

The various methods of using the coupling device of the present invention can be used for any human or animal subject to which ultrasonic energy can be applied.

The various methods of using the coupling device of the present invention can involve applying ultrasonic energy to a surface of the subject that is at or near a joint of the subject. These methods can be used for various joints, including, for example, a finger joint, a shoulder joint, a hip joint, a knee joint, an ankle joint, a toe joint, a wrist joint, and an elbow joint.

The various methods of using the coupling device of the present invention can involve applying ultrasonic energy to a surface at or near a vertebral column area of the subject, including, vertebral column areas the cervical vertebrae, thoracic vertebrae, lumbar vertebrae, sacrum, and coccyx.

The various methods of using the coupling device of the present invention can involve applying ultrasonic energy to a surface at or near a muscle of the subject.

ADDITIONAL DISCLOSURE

The ultrasound coupling device of the present invention has various attributes, as described more fully herein. Without meaning to limit the present invention to a particular embodiment, provided below are various attributes of the present invention.

Ultrasound Coupling Device

Embodiment 1

One embodiment (referred to as Ultrasound Coupling Device Embodiment 1) is illustrated in FIGS. 7 and 8. In this embodiment, a material such as a non-woven fabric can be used in combination with a semi-permeable membrane to allow placement of an ultrasound transducer on an object. The transducer can be secured in place internally to the patch, and the semi-permeable membrane window allows efficient coupling of ultrasound energy from the transducer into the object (e.g., a human). This embodiment is generally configured in a "patch" or "bandage" configuration. The patch may be in a pouch that can prevent the gel inside of the pouch from drying out. Further, the front surface of the patch (the side that contacts the body) can have a laminate coating/plastic film that may be removed to expose the adhesive as well as the semi-permeable membrane. This mechanism is similar to how an adhesive bandage is produced.

Device Attributes. Ultrasound Coupling Device Embodiment 1 has various attributes (see FIG. 7), including, for example, the following: (i) it can be made from disposable, soft, comfortable, flexible materials; (ii) it can be used in combination with a flat, concave, or convex low-profile transducer; (iii) it can include a semi-permeable membrane that is configured to be "leaky," thereby allowing the contact surface to become slightly wet, and allowing efficient ultrasound transmission; (iv) it can be made from a soft, non-woven material, similar to a bandage with adhesive on the front surface to secure the device into place; (v) the semi-permeable membrane can be thin for efficient ultrasound energy transfer, and to allow liquid to wet the contact surface of the body of ultrasound transmission (e.g., a human); (vi) the semi-permeable membrane may be wet with saline, gel, or any other aqueous medium that allows efficient ultrasound coupling from the transducer into the body (e.g., a human); (vii) the acoustic window of the semi-permeable membrane can be such that it is the face of the patch, and may be designed in various configurations to accommodate ultrasound transducers; and (viii) the acoustic window may be optically transparent to allow light to pass through easily.

As shown in FIG. 8, Ultrasound Coupling Device Embodiment 1 can be used in combination with an ultrasound transducer. FIG. 8 shows how this embodiment of the coupling device works with an ultrasound transducer. The coupling device (e.g., patch) is placed on the object and the ultrasound transducer is inserted into the patch. Extra gel/acoustic coupling medium may be wiped away after the transducer is inserted.

Ultrasound Coupling Device

Embodiment 2

One embodiment is further referred to as Ultrasound Coupling Device Embodiment 2. This embodiment is similar to Ultrasound Coupling Device Embodiment 1 (described herein). However, in Ultrasound Coupling Device Embodiment 2, the device is not in the form of a patch but of a semi-permeable membrane that may be used to effectively transmit ultrasound from an ultrasound transducer into a body (e.g., a human) without the need for applying ultrasound gel or other coupling medium to the surface of the object. Therefore, the invention reduces the aggravation and discomfort of using ultrasound devices.

Device Attributes. Ultrasound Coupling Device Embodiment 2 has various attributes, including, for example, the following: (i) this device can have a broad impact on improving ultrasound imaging and therapy applications by removing the gel; (ii) the transducer can slip into the device; (iii) the device can be filled with ultrasound gel; (iv) the membrane of the device can be configured to leak fluid to allow the object being touched to get "wet," thereby allowing efficient ultrasound energy transmission; (v) the device may take the form of various shapes to accommodate many types of ultrasound transducers; (vi) once the transducer is inserted, the elastic nature of the device can keep the liquid/gel in place; (vii) the device may be used in any spatial direction; (viii) the device may be disposable; (ix) the device may be refilled with acoustic gel/coupling medium; and (x) the membrane can be optically transparent/translucent to allow light to penetrate it.

While several aspects of the present invention have been described and depicted herein, alternative aspects may be effected by those skilled in the art to accomplish the same objectives. Accordingly, it is intended by the appended claims to cover all such alternative aspects as fall within the true spirit and scope of the invention.

What is claimed is:

1. An ultrasound coupling device comprising:
    a coupling compartment comprising a chamber having a continuous side wall and an opening on a first end, wherein said ultrasound coupling device is configured for operative coupling with a low-profile ultrasound transducer and an ultrasound conductive medium so as to apply ultrasonic energy to a subject, wherein said continuous side wall is configured to hold said low-profile ultrasound transducer completely within the chamber so that a front ultrasound emitting surface of the low-profile ultrasound transducer faces outward toward the chamber opening but does not extend beyond the first end of the continuous side wall of the chamber, said front ultrasound emitting surface configured to control the direction and wave pattern of ultrasonic energy emitted from the low-profile ultrasound transducer, wherein said continuous side wall is configured to hold the ultrasound conductive medium within the chamber and operative to keep the ultrasound conductive medium in simultaneous contact with the subject and with at least a portion of the front ultrasound emitting surface of the low-profile ultrasound transducer, and wherein said continuous side wall is configured so that when said ultrasound coupling device is operatively coupled together with said low-profile ultrasound transducer and the ultrasound conductive medium, the first end of the continuous side wall is in contact with the subject so as to keep a quantity of the ultrasound conductive medium within the chamber.

2. The ultrasound coupling device according to claim 1, wherein said chamber has a second end opposite to the first end, said second end comprising a barrier effective to form a cavity region within the chamber between the second end of the chamber and the low-profile ultrasound transducer.

3. The ultrasound coupling device according to claim 1, wherein said continuous side wall further comprises an opening configured to allow a cable connected to the low-profile ultrasound transducer to extend outside of the chamber.

4. The ultrasound coupling device according to claim 3, wherein said opening comprises cable support extension that extends outward from the continuous side wall and includes a passage way for the cable.

5. The ultrasound coupling device according to claim 1, wherein the coupling compartment further comprises a flange region extending outward from at least a portion of the continuous side wall of the chamber.

6. The ultrasound coupling device according to claim 5, wherein at least a portion of the flange region comprises an adhesive material effective to keep the coupling device in place on the surface of the subject.

7. The ultrasound coupling device according to claim 5 further comprising:

a semi-permeable membrane that covers the opening of the first end of the chamber, wherein said semi-permeable membrane is effective to allow the ultrasound conductive medium to be released from the coupling compartment's first end when pressure is applied to the semi-permeable membrane.

8. The ultrasound coupling device according to claim 7 further comprising:

a covering sheet attached to the flange region and configured to cover the semi-permeable membrane.

9. The ultrasound coupling device according to claim 8, wherein said covering sheet is configured to be manually removable from the flange region to expose the semi-permeable membrane.

10. The ultrasound coupling device according to claim 7, wherein said semi-permeable membrane is optically transparent and/or translucent, thereby allowing light emitted from the low-profile ultrasound transducer to penetrate through the semi-permeable membrane.

11. The ultrasound coupling device according to claim 1, wherein at least a portion of the continuous side wall of the chamber is configured to allow the low-profile ultrasound transducer to be inserted into the chamber through said at least portion, rather than through the first end or second end of the chamber.

12. The ultrasound coupling device according to claim 1, wherein the ultrasound conductive medium is selected from the group consisting of a gel, a hydrogel, an acoustic gel, saline, a low-viscosity liquid, and the like.

13. An ultrasound apparatus comprising:

at least one low-profile ultrasound transducer; and at least one ultrasound coupling device according to claim 1, wherein said at least one ultrasound coupling device is operatively coupled to the at least one low-profile ultrasound transducer, thereby forming a transducer/coupling device unit.

14. The apparatus according to claim 13 further comprising:

a holder component a wearable apparatus for holding the transducer/coupling device unit in place on a surface of a subject.

15. The apparatus according to claim 14, wherein said holder component holds one or more transducer/coupling device units in place on a surface of a subject.

16. The apparatus according to claim 14, wherein said holder component is a wrap.

17. The ultrasound coupling device according to claim 1, wherein the coupling compartment further comprises an enabler component which enables the operation of the low-profile ultrasound transducer.

* * * * *